United States Patent [19]

Ramachandran et al.

[11] Patent Number: 5,126,463

[45] Date of Patent: Jun. 30, 1992

[54] PROCESS FOR THE PRODUCTION OF ANHYDRIDES

[75] Inventors: Ramakrishnan Ramachandran, Allendale; Arthur I. Shirley, South Orange; Lien-Lung Sheu, Scotch Plains, all of N.J.

[73] Assignee: The BOC Group, Inc., New Providence, N.J.

[21] Appl. No.: 607,198

[22] Filed: Oct. 31, 1990

[51] Int. Cl.$^5$ ............................................. C07D 307/60
[52] U.S. Cl. .................................. 549/262; 549/231; 549/232; 549/233; 549/247; 549/248; 549/249; 549/256; 549/257; 549/258; 549/259; 549/260; 549/261
[58] Field of Search ............... 549/231, 232, 233, 247, 549/248, 249, 256–262

[56] References Cited

U.S. PATENT DOCUMENTS

| | | | |
|---|---|---|---|
| 3,904,652 | 9/1975 | Frank | 549/259 |
| 4,231,943 | 11/1980 | Paradis et al. | 260/346.75 |
| 4,352,755 | 10/1982 | Higgins et al. | 549/259 |
| 4,515,973 | 5/1985 | Wrobleski | 549/259 |
| 4,562,268 | 12/1985 | Wrobleski et al. | 549/259 |
| 4,699,985 | 10/1987 | Bither, Jr. | 549/259 |
| 4,987,239 | 1/1991 | Ramachandran et al. | 549/262 |

*Primary Examiner*—Cecilia Shen
*Attorney, Agent, or Firm*—Robert I. Pearlman; Coleman R. Reap

[57] ABSTRACT

This invention provides a process for the production of an anhydride by the vapor phase reaction of a hydrocarbon with substantially pure oxygen in the presence of a suitable catalyst. In the improved process, the anhydride product is removed, carbon monoxide, present in the reactor effluent as a by-product, is oxidized to carbon dioxide and part of the gaseous effluent, comprised mainly of carbon dioxide and unreacted hydrocarbon, is recycled to the reactor. Removal of carbon monoxide from the recycle stream reduces the hazard of a fire or explosion in the reactor or associated equipment. The use of carbon dioxide as the principal diluent increases heat removal from the reactor, thereby increasing the production capacity of the reactor.

27 Claims, 1 Drawing Sheet

5,126,463

PROCESS FOR THE PRODUCTION OF ANHYDRIDES

FIELD OF THE INVENTION

The present invention is directed to a process for producing an anhydride from a hydrocarbon and an oxygen-containing gas in the presence of a suitable catalyst, and more particularly to a process for achieving increased production while reducing or eliminating the hazard of an explosion or fire in an existing or new vapor phase reactor system in which an anhydride is produced from a hydrocarbon and oxygen.

BACKGROUND OF THE INVENTION

Cyclic anhydrides are produced commercially by the oxidation of an appropriate hydrocarbon in the vapor phase over a suitable catalyst. For example, maleic anhydride is produced commercially by the vapor phase oxidation of benzene or straight-chain $C_4$ hydrocarbons (hydrocarbons containing four carbon atoms), such as n-butene or butadiene, with an oxygen-containing gas, over a vanadium-phosphorus oxide catalyst. Air is generally used as the oxygen-containing gas, because of its low cost and ready availability. The reaction can be carried out in any suitable reactor, such as a fixed bed, fluidized bed, or transport bed reactor, and it produces the anhydride, and generally carbon monoxide (CO), carbon dioxide ($CO_2$), water, and smaller amounts of other partially oxidized by-products. The reaction equipment train generally consists of a reactor, in which the anhydride is produced, a scrubber, in which the maleic anhydride is scrubbed from the reactor effluent gases by means of water or other solvent for the anhydride, and means for further treating the scrubbed effluent gases.

In the past it was common to practice the above-described process on a single pass basis with the conversion of hydrocarbon to the desired anhydride product being maximized. This resulted in a low overall efficiency, since the selectivity to maleic anhydride was below the maximum. Consequently, the scrubber effluent gas contained considerable amounts of CO and $CO_2$, in addition to unreacted hydrocarbon. These products were usually incinerated, so that the only return realized from them was heat value. In later processes a portion of the scrubber effluent gas was recycled, the conversion of the hydrocarbon feedstock was lowered and the selectivity of hydrocarbon conversion to maleic anhydride was increased. The remainder of the effluent was purged from the system to prevent the build-up of CO, $CO_2$ and nitrogen (introduced into the system when air is used as the source of oxygen). These improvements resulted in a reduced "per pass" conversion, but the overall efficiency of the process was increased.

Federal Republic of Germany (FRG) Patent Application Disclosure 25 44 972 discloses a maleic anhydride manufacturing process in which the reactor feed comprises $C_4$ hydrocarbons, air, CO and $CO_2$. In the process of this patent, maleic anhydride is recovered from the reactor effluent gas stream and a portion of the remaining stream is recycled. This patent also teaches recovering butane by temperature swing adsorption form the non-recycled gas stream and recycling the recovered butane to the reactor.

U.S. Pat. No. 4,352,755 discloses a recycle process for the vapor phase manufacture of maleic anhydride by reacting a straight-chain $C_4$ hydrocarbon with oxygen in the presence of $CO_2$. In the process disclosed in this patent the gaseous mixture may contain up to 30 volume percent of carbon dioxide as the inert diluent and contains at least 25 volume percent $C_4$ hydrocarbon.

Recycling a portion of the effluent gas from gas phase anhydride reactors increases the capital costs compared to single pass processes since the size of the reactor and associated equipment must be increased to handle the increased volumes of CO, $CO_2$ and nitrogen resulting from the recycling step. The problem is intensified when low heat capacity gases such as nitrogen are used as diluents because greater gas flows are necessary to provide adequate heat removal to prevent overheating.

Another problem associated with the gas phase production of an anhydride by the oxidation of hydrocarbons with an oxygen-containing gas is that since the reaction is carried out at elevated temperatures, there is an ever-present danger of a fire or an explosion in the reactor or the equipment or pipelines associated with the reactor. Accordingly, the concentrations of the reactants in the system are maintained such that the mixture is kept outside of the flammability range. Although nitrogen serves to reduce the flammable mixture range when air is used as the source of oxygen for the reaction, the flammable mixture range for hydrocarbon-air mixtures is still quite broad. Consequently, it has been customary to operate gas phase anhydride reactors at low hydrocarbon levels so that the reaction mixture will remain outside of the flammable range.

U.S. Pat. No. 3,904,652 teaches a gas phase maleic anhydride manufacturing process in which oxygen is used as the oxidizing gas and an inert gas, such as nitrogen, argon, helium or a lower hydrocarbon is fed into the reactor with the n-butane and oxygen, the inert gas serving as a diluent to reduce the concentrations of oxygen and butane in the reactor to below the point at which they form a flammable mixture. In the disclosed process, a portion of the gaseous effluent, which contains, in addition to butane, carbon monoxide, carbon dioxide and the inert gas, is recycled. One of the disadvantages of a process such as the one disclosed in this patent is that recycling carbon monoxide increases the fire and explosion hazard because carbon monoxide itself is highly flammable.

Because of ever increasing safety concerns and energy costs, there are continuing efforts by industry to make chemical processes involving oxygen and flammable compounds less hazardous and more economical to operate.

OBJECTS OF THE INVENTION

It is an object of the invention to reduce or eliminate the fire and explosion hazards associated with gas phase anhydride manufacturing processes.

It is another object of the invention to improve the cost effectiveness of gas phase cyclic anhydride manufacturing processes.

It is another object to increase the productivity of gas phase cyclic anhydride production reactors.

It is another object of the invention to provide a novel system for producing cyclic anhydrides by the vapor phase oxidation of hydrocarbons.

These and other objects and advantages of the invention will become apparent from the following description and examples.

SUMMARY OF THE INVENTION

The present invention provides an improvement in a recycle process and apparatus for manufacturing a cyclic anhydride by the vapor phase oxidation of a hydrocarbon with oxygen in the presence of a suitable catalyst. In such a process the reactor effluent contains the anhydride as the main product, carbon monoxide and carbon dioxide as by-products and, in most cases, unreacted hydrocarbon. The invention includes the step of converting some or all of the carbon monoxide in the effluent stream to carbon dioxide by contacting it with an appropriate catalyst, and recycling a portion of the carbon dioxide with the unreacted hydrocarbon.

According to one aspect of the invention one or more hydrocarbons such as o-xylene, naphathalene, benzene and straight-chain hydrocarbons containing four carbon atoms are contacted with an oxygen-containing gas in a suitable oxidation reactor and in the presence of carbon dioxide as a diluent, to produce a gaseous product stream containing a cyclic anhydride, such as phthalic anhydride or maleic anhydride, the specific anhydride produced depending upon which hydrocarbon is reacted. The hydrocarbon oxidation reactor product stream also contains carbon monoxide and carbon dioxide, and generally unreacted hydrocarbons(s), oxygen, and possibly small amounts of other reaction by-products. The gaseous product stream leaving the oxidation reactor is treated in a cyclic anhydride removal means, such as a scrubber, wherein it is contacted with a liquid solvent which removes substantially all of the cyclic anhydride from the gas stream. The cyclic anhydride-containing liquid solution is discharged from the scrubber and treated to recover the cyclic anhydride. Prior to or following the cyclic anhydride removal step all or a portion of the gaseous product stream is treated in a carbon monoxide converter to convert some or all of the carbon monoxide in the stream to carbon dioxide. For this step a catalyst is selected which oxidizes the carbon monoxide but which does not, to any great extent, oxidize the unreacted hydrocarbon present in the stream. Part of the carbon dioxide is subsequently removed from the stream and the remainder of the stream is recycled to the hydrocarbon oxidation reactor.

In a preferred embodiment of the process aspect of the invention the oxygen-containing gas is substantially pure oxygen and the principal diluent in the system is carbon dioxide. In another preferred embodiment the concentration of carbon dioxide present in all parts of the reaction system is sufficiently high to along prevent the formation of a flammable mixture in the system. In yet another preferred embodiment the hydrocarbon oxidation step is carried out in a fixed bed reactor. In other preferred embodiments carbon dioxide is removed from the gaseous product stream by purging, adsorption or absorption. When the process is used to produce maleic anhydride, the preferred feed hydrocarbons are the four-carbon straight-chain hydrocarbons. The most preferred straight-chain hydrocarbon is n-butane. Orthoxylene is the preferred feed hydrocarbon for the manufacture of phthalic anhydride.

Another novel aspect of the invention is the apparatus in which the process of the invention is carried out. The apparatus comprises a hydrocarbon oxidation reactor, an anhydride scrubber, a carbon monoxide converter and a carbon dioxide separator. The hydrocarbon oxidation reactor may be any suitable reactor, such as a fixed bed reactor, a fluidized bed reactor, a moving bed reactor or a transport bed reactor. The carbon monoxide converter may be the fixed bed or fluizided bed type and it can be located either before or after the anhydride scrubber in the equipment train. The carbon dioxide separator may be any suitable means normally used to remove carbon dioxide from a gas mixture, such as an adsorber, an adsorber or a gas purge means.

In preferred embodiments of this aspect of the invention, the hydrocarbon oxidation reactor and the carbon monoxide converter are both fixed bed and the carbon dioxide removal means is an adsorber or a gas purge device. In most preferred embodiments the hydrocarbon oxidation reactor is a fixed bed reactor and the carbon dioxide separator is a pressure swing adsorber.

DETAILED DESCRIPTION OF THE INVENTION

Figure 1:
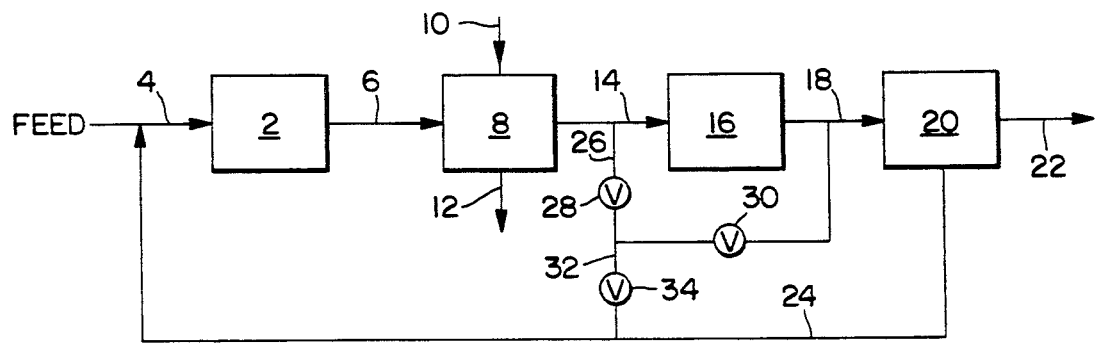
FIG. 1 illustrates, in a block diagram, a system for producing an anhydride in accordance with one embodiment of the present invention

According to the process of the invention, a hydrocarbon is reacted with oxygen in the vapor state in a reaction zone containing a suitable catalyst and in the presence of carbon dioxide as the principal diluent to produce a gaseous product stream containing a cyclic anhydride and carbon monoxide, the cyclic anhydride is removed from the gaseous product stream, all or a portion of the carbon monoxide in the product stream is oxidized to carbon dioxide, a portion of the carbon dioxide is removed from the stream and the resulting stream is recycled to the hydrocarbon reaction zone.

The invention can be better understood from the accompanying drawings, in which the same reference numeral is used to designate the same or similar equipment in the various figures. Auxiliary equipment, including valves, compressors and heat exchangers, which are unnecessary for an understanding of the invention have been omitted from the drawings to simplify discussion of the invention.

Considering first FIG. 1, the apparatus of this embodiment includes a hydrocarbon oxidation reactor 2 having a feed inlet means 4 and a product outlet 6. Product outlet 6 is connected to an anhydride recovery unit, such as scrubber 8, which receives a scrubbing liquid through inlet 10 and discharges a liquid product through outlet 12. Scrubber 8 is also monoxide converter 16. Converter 16 discharges oxidized gas through line 18, which is connected to carbon dioxide separator 20. Separator 20 is provided with a waste gas discharge line 22, and it is also connected via recycle line 24 with feed inlet means 4. The system illustrated in FIG. 1 is also equipped with a bypass line 26, controlled by valves 28 and 30, and bypass line 32, controlled by valve 34.

Figure 2:
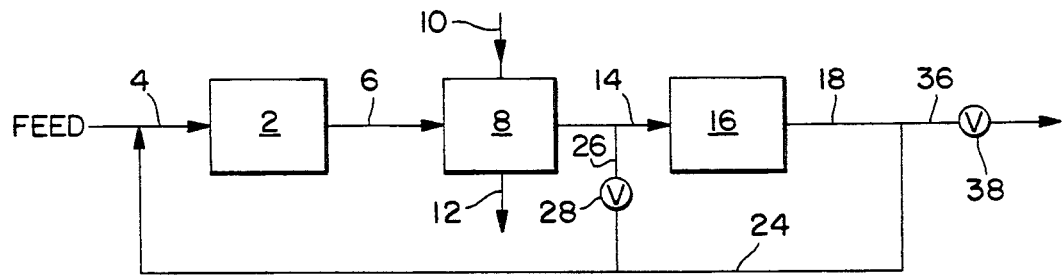
FIG. 2 illustrates, in a block diagram, a system for producing an anhydride in accordance with a second embodiment of the invention.

FIG. 2 illustrates a variation of the system of FIG. 1. This system is substantially the same as the FIG. 1 system, however in the FIG. 2 system the carbon dioxide separator 20 of FIG. 1 is replaced by a purge line 36 which is controlled by valve 38.

Figure 3:
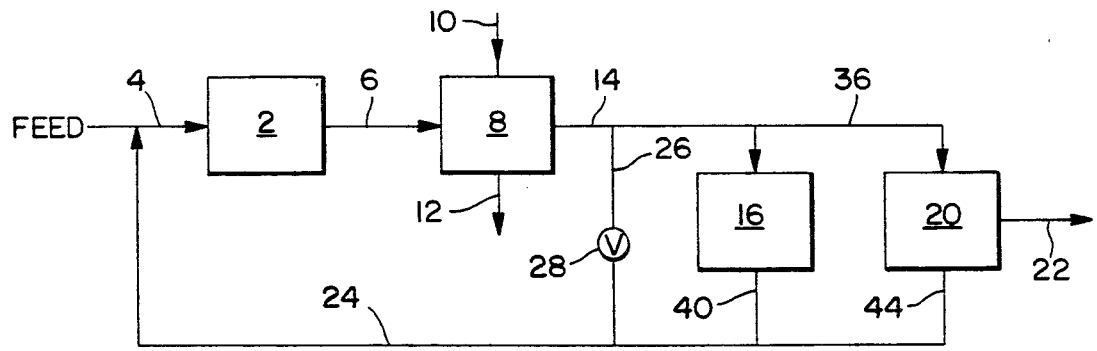
FIG. 3 illustrates, in a block diagram, a modified embodiment of the system illustrated in FIG. 1.

FIG. 3 illustrates another variation of the system of FIG. 1. In the embodiment of FIG. 3, carbon monoxide converter and 16 and carbon dioxide separator 20 are arranged in parallel and each of these units can receive as feed a portion of the effluent from scrubber 8. Converter 16 receives scrubber effluent via line 14 and discharges oxidized gas for recycle to reactor 2 via lines 40 and 24; and separator 20 receives scrubber effluent via lines 14 and 36 and discharges a waste stream to vent through line 22 and a stream for recycle to reactor 2 via lines 44 and 24. The system of FIG. 3 is also equipped with a bypass line 26, controlled by valve 28. Flow through converter 16, separator 20 and bypass line 26 can be adjusted to any desired rates.

Reactor 2 may be any suitable reactor but it is usually of the fixed, moving fluidized, or transport catalyst bed design. Reactor 2 may be equipped with heat exchange means to remove heat developed in the reaction, which is exothermic. The specific design details of suitable reactor are well known and they form no part of the present invention. Anhydride recovery unit 8 is typically a conventional gas scrubber, i.e. an absorber, usually of the packed bed design, and it is here illustrated as equipped with means for spraying water or an aqueous or nonaqueous liquid on the product gas entering this unit from reactor 2. Converter 16, like reactor 2, may be of any suitable design. In preferred embodiments of the invention converter 16 is a fixed bed reactor. Although converter 16 is positioned downstream of the anhydride scrubber in the drawings, it can be located upstream of the anhydride scrubber, or, if desired, it can even be incorporated in reactor 2. The purpose of carbon dioxide separator 20 is to remove carbon dioxide and other inert gases from the system, and this unit can be any device which will accomplish this result. Separator 20 is usually an adsorber or an absorber. In preferred embodiments of the invention separator 20 is a pressure swing adsorption (PSA) unit or a temperature swing adsorption (TSA) unit.

In the process of the invention, feed, comprising a suitable hydrocarbon, an oxygen-containing gas and the recycle gas stream, enters reactor 2 through inlet means 4, which may comprise a single inlet line through which a mixture of the gaseous reactants and diluents is introduced into reactor 2, or it may comprise several individual inlet lines for separately introducing the reactants into the reactor. The particular inlet arrangement will generally depend upon the type of reactor used for practicing the invention. In fixed bed reactor systems the components of the feed are generally mixed before they enter the reactor and are thus fed into the reactor through a single line, whereas in fluidized bed reactor systems, the components are usually separately fed into the reactor.

The hydrocarbon used in the reaction will, of course, depend upon which anhydride is to be produced. If it is desired to produce phthalic anhydride, the hydrocarbon feed is preferably o-xylene or naphthalene, and if maleic anhydride is desired, the hydrocarbon feed is generally benzene or straight-chain hydrocarbons containing four carbon atoms ($C_4$ hydrocarbons). Straight-chain $C_4$ hydrocarbons are currently preferred over benzene for the manufacture of maleic anhydride because of the high cost of benzene. The straight-chain $C_4$ hydrocarbons comtemplated for use in the invention are n-butane, butene and butadiene. n-Butane is the most preferred hydrocarbon for maleic anhydride manufacture because it is less expensive than the unsaturated $C_4$ hydrocarbons, the latter being more valuable because of their usefulness as monomers. Commercial grade n-butane often contains other hydrocarbons, such a i-butane, but these impurities are not objectionable because they do not interfere with the manufacture of maleic anhydride from n-butane. The process of the invention will be described with particular reference to the manufacture of maleic anhydride from n-butane, but the invention is not limited thereto.

The oxygen-containing gas may be air, oxygen-enriched air, other oxygen-inert gas mixtures or substantially pure oxygen. By oxygen-enriched air is meant air that contains more oxygen than is naturally present in air. Oxygen-inert gas mixtures include oxygen-nitrogen mixtures, oxygen-argon mixtures, oxygen-carbon dioxide mixtures, etc. Pure oxygen is preferred since its use avoids the introduction of inert gases, such as nitrogen and argon, into the system and the subsequent need to remove excess quantities of these inert gases from the product gas stream to prevent their buildup in the system.

It can be appreciated that to fully realize the main benefit of the invention, i.e. the oxidation of carbon monoxide to carbon dioxide, carbon dioxide must be recycled as a diluent in the system. In the preferred embodiment carbon dioxide is present in the system as the principal inert diluent, i.e. carbon dioxide is present in the reaction system at a concentration greater than any other inert gaseous component. Thus, other inert gaseous components, such as nitrogen, argon, water vapor and nonreactive compounds, including nonreactive hydrocarbons, may be present in the system, but, on a volume basis, the concentration of each of these other inert components in the system is less than the concentration of carbon dioxide in the system. An "inert gaseous component" is one that does not react under the conditions existing in the system. The carbon dioxide concentration in the system is preferably maintained sufficiently high so that it alone will prevent the gases in any part of the system from forming a flammable mixture. In the preferred embodiment, carbon dioxide comprises at least 60 volume percent, and in the most preferred embodiment carbon dioxide comprises at least 80 volume percent of the total gases in the system.

In the startup operation of the process of the invention, carbon dioxide or any other inert gas can be introduced into the system with the feed to insure that the gas mixture is and remains outside of the flammable range. It is often convenient to use an inert gas other than carbon dioxide in the startup operation. For example, if air is used as the oxygen source during the startup period, the nitrogen component of the air can serve as the diluent until the carbon dioxide level increases to the desired level. Then, in the preferred embodiment, the air can be gradually replaced by substantially pure oxygen or oxygen-enriched air. The carbon dioxide can be easily maintained in the desired range by controlling the amount of carbon dioxide recycled.

The feed gases entering reactor 2 contact the catalyst and react to form the product gases. Any of the well known catalyst for oxidizing hydrocarbons to cyclic anhydrides under the specified conditions can be used in the process of the invention. Suitable catalysts include vanadia-based catalysts, such as vanadium oxides, vanadium/molybdenum oxides, vanadium/phosphorus oxides and vanadium/titanium oxides. These catalysts and their use are conventional and well known to those skilled in the manufacture of anhydrides. The specific hydrocarbon oxidation catalysts used in the process of the invention do not form a part of the invention.

The conditions of the hydrocarbon oxidation are well known and form no part of the invention. Typically, the oxidation reaction is conducted at a temperature of from about 250° C. to about 600° C., and usually from about 300° to about 500° C., and at low pressures, typically in the range of from about 2 to about 50 psig, and usually from about 3 to about 30 psig. The reactants are generally passed through the reactor at a velocity in the range of from about 0.5 to about 5.0 ft./sec. In the manufacture of maleic anhydride from n-butane and phthalic anhydride from o-xylene, the volume ratio of oxygen to n-butane or to o-xylene in the feed is suitably in the range of about 0:3:1 to about 50:1.

The product gas stream leaving reactor 2 contains the cyclic anhydride as the main product, and carbon dioxide and carbon monoxide as by-products. As noted above, the product stream generally also contains unreacted butane and oxygen, and may contain small amounts of other by-products, impurity gases and non-reactive hydrocarbons. In the embodiments illustrated in the drawings, the product gas stream leaves reactor 2 via line 6 and enters scrubber 8. The purpose of scrubber 8 is to remove the cyclic anhydride from the hydrocarbon reactor effluent gas. In scrubber 8 the product gases are intimately contacted with a solvent for the anhydride. The solvent dissolves substantially al of the anhydride out of the product gas stream and this solution leaves scrubber 8 via line 12. It is usually further treated to recover the anhydride. The scrubbed gas stream leaves scrubber 8 through line 14 and enters carbon monoxide converter 16.

The purpose of carbon monoxide converter 16 is to convert carbon monoxide produced in the hydrocarbon oxidation reaction to carbon dioxide in order to prevent the build-up of carbon monoxide in the system. Converter 16 contains a catalyst which promotes the oxidation of carbon monoxide to carbon dioxide. Any catalyst that will promote the oxidation of carbon monoxide to carbon dioxide without significantly affecting the hydrocarbon present in the system can be used in converter 16. Among the catalysts suitable for use in converter 16 are the mixed copper-manganese oxides. These compositions may be used as is or mounted on a suitable substrate, such as silica. As will become clear from the discussion which follows, the unreacted hydrocarbon and carbon dioxide leaving converter 16 are recycled to reactor 2 so that the process can be optimized. Accordingly, if carbon monoxide (which is also recycled with the unreacted hydrocarbon) is not removed, as by conversion to carbon dioxide, the concentration of carbon monoxide in the system will increase and eventually reach the level at which a flammable mixture exists. To avoid this problem, it is sufficient to remove an amount of carbon monoxide equivalent to the amount that is produced in reactor 2 in each pass. Thus, converter 16 can be a relatively small reactor.

Generally, about 5 to about 20 mole percent of the hydrocarbon entering reactor 2 is converted to carbon dioxide and about 5 to about 20 mole percent of it is converted to carbon dioxide in converter 16 is substantially equal to the amount of carbon monoxide produced in reactor 2, the total amount of carbon dioxide produced in the reaction process is about 20 to about 40 mole percent, based on the amount of hydrocarbon entering reactor 2. Thus, it can be appreciated that an advantage of the invention is that the concentration of carbon dioxide can be quickly brought up to the desired operating level during startup.

In some cases it may not be necessary to pass all of the scrubbed gas through converter 16 to effect the desired degree of carbon monoxide conversion. In such cases a portion of the scrubbed gas effluent in line 14 can be bypassed around converter 16 through line 26 by opening valves 28 and 30 and closing valve 34 in line 32. In other cases it may be desired to permit some of the scrubbed gas in line 14 to bypass converter 16 and separator 20. In this case valves 28 and 34 are opened and valve 30 is closed. Thus, the system can be operated with all or a portion of the scrubbed gas in line 14 passing through reactor 16.

After the carbon monoxide oxidation step, the gas stream leaves converter 16 through line 18 and enters separator 20. Separator 20 serves the purpose of removing carbon dioxide and other inert gases in excess of the amounts which it is desired to recycle. For example, when air is used as the source of oxygen, carbon dioxide in excess of the amount that it is desired to recycle, nitrogen and argon are removed from the system in separator 20. To prevent the buildup of nitrogen and argon in the system when air is used as the source of oxygen, it is generally necessary to remove from the system substantially all of the nitrogen and argon entering reactor 2 with the fresh feed. This can be easily accomplished by operating separator 20 in such a manner that nitrogen and argon pass through the separator and hydrocarbon and some or all of the carbon dioxide are absorbed or adsorbed. Nitrogen, argon and excess carbon dioxide are removed from separator 20 via line 22 and the remaining carbon dioxide, unreacted hydrocarbon and a small amount of carbon monoxide are recycled to reactor 2 through line 24. Line 24 may be connected to line 4, as shown in the drawings, or it may be connected directly to reactor 2.

As indicated above, separator 20 can be any means for separating unreacted hydrocarbon and carbon dioxide from the effluent from converter 16, but in the preferred embodiment this unit is a pressure swing adsorber. Pressure swing adsorption is a well known process for separating the components of a mixture of gases by virtue of the difference in the degree of adsorption among them on a particulate adsorbent retained in a stationary bed. Typically, two or more such beds are operated in a cyclic process comprising adsorption under relatively low pressure or vacuum. The desired component or components may be obtained during either of these stages. The cycle may contain other steps in addition to the fundamental steps of adsorption beds cycled 180° out of phase to assure a pseudo continuous flow of desired product. While it is conventional for the adsorption step of a PSA cycle to be carried out under pressure, it can run at ambient pressure with desorption under vacuum.

In a preferred embodiment of the invention, substantially pure oxygen is used as the oxidant and carbon dioxide is used as the principal diluent gas. In this case very little or not nitrogen is introduced into the system and the gas stream entering separator 20 is comprised substantially of unreacted hydrocarbon, carbon dioxide and carbon monoxide. Separator 20 then serves to remove only a small amount of carbon dioxide from the system, and the remaining part of the gas stream entering separator 20, comprised of carbon dioxide, unreacted hydrocarbon and carbon monoxide, is recycled to reactor 2. In some cases it may not be necessary to pass all of the carbon dioxide through separator 20. In such cases part of the effluent from converter 16 can be discharged directly to recycle line 24 by opening valves 30 and 34 and closing valve 28. The system can also be operated with valves 28, 30 and 34 open, if desired.

In operating the process of the invention in accordance with the embodiment of FIG. 2, a portion of the effluent gas stream from converter 16 is purged from the system through line 36 by opening valve 38, and the remainder of the effluent is recycled to reactor 2 via line 24. Since the gas being purged has the same composition as the gas being recycled, the process of this embodiment is most convenient when the oxidant is substantially pure oxygen. In this case substantial amounts of nitrogen will not be present in the gas being recycled to reactor 2. As was the case with the FIG. 1 embodiment, a portion of the scrubbed gas leaving scrubber 8 can be bypassed around converter 16 via line 26 by opening valve 28.

In practicing the process of the invention in the system of FIG. 3, part of the effluent from scrubber 8 is passed through converter 16 to oxidize the desired amount of carbon monoxide to carbon dioxide and part of the scrubber effluent is sent to separator 20 to remove the desired amount of carbon dioxide and other inert gases, if any are present, from the system through line 22. The effluent from converter 16 (in line 40) and the stream selected for recycle from separator 20 (in line 44) are combined and returned to reactor 2 through line 24. In some situations it may not be necessary to pass all of the scrubber effluent through converter 16 and separator 20. In such cases a part of the effluent is directly recycled to reactor 2 via lines 26 and 24 by opening valve 28.

It will be appreciated that it is within the scope of the present invention to utilize conventional equipment to monitor and automatically regulate the flow of gases within the system so that it can be fully automated to run continuously in an efficient manner.

Several advantages are achieved by the practice of the invention. For example, use of the carbon monoxide converter permits the process to be run without discharging carbon monoxide to the atmosphere; eliminates excess carbon monoxide from the reaction system, thereby reducing the danger of fire or explosion in the equipment used in the process; and shortens the time required to increase the carbon dioxide concentration in the system to the desired operating level. Using carbon dioxide as the inert diluent increases the production capacity of the reaction system because the relatively high heat capacity of carbon dioxide enables the reaction to be run with less inert gas present. Accordingly, the reactants can be fed to the reactor at a higher flow rate. Other advantages of the process of the invention are its simplicity, ease of operation and low capital and operating costs. Additionally, the process can be run at a relatively low per pass conversion of the feed hydrocarbon to the desired product to achieve substantially improved selectivity.

The invention is further illustrated by the following examples in which parts, percentages and ratios are on a volume basis, unless otherwise indicated.

EXAMPLE I

A gas mixture comprised of the components listed as feed in TABLE I was fed into a one-half inch carbon steel reactor containing 2 grams of mixed copper oxide-manganese oxide catalyst sold by Carus Chemical Company under the trademark Carulite* 200. The catalyst bed occupied a volume of 2.2 cc in the reactor. The gas mixture was heated to a temperature of 200° C. and was fed into the reactor at a specific flow rate of 67.6 reciprocal minutes. The results of this run are tabulated in TABLE I.

TABLE I

| Component | Feed cc/min | Feed Vol. % | Effluent cc/min | Effluent Vol % |
|---|---|---|---|---|
| $CO_2$ | 139.73 | 93.97 | 143.81 | 97.85 |
| $O_2$ | 2.77 | 1.86 | 0.51 | 0.35 |
| CO | 3.49 | 2.35 | 0.03 | 0.02 |
| $C_4H_{10}$ | 2.72 | 1.82 | 2.62 | 1.78 |
| Total | 148.70 | 100.00 | 146.97 | 100.00 |

TABLE I shows that 99.16 volume percent of the carbon monoxide fed to the reactor was converted to carbon dioxide, while the extent of the hydrocarbon conversion is minimal.

EXAMPLE II

A vapor phase maleic anhydride production run was simulated in a fixed bed reactor based on the results obtained in the experiment of EXAMPLE I. The reactor system was similar to the system of FIG. 3. The simulated feed to the hydrocarbon reactor is comprised of the Fresh Feed component and the Recycle Stream component. The reaction is simulated based on the use of a vapor phase hydrocarbon reactor containing monoxide convertor containing a fixed bed catalyst comprised of Carulite* 200 and a pressure swing adsorber containing a molecular sieve adsorption bed. The various flow rates and projected results are tabulated in TABLE II.

TABLE II

| Component | Fresh Feed Moles | Fresh Feed Vol % | Feed to MA Reactor (1) Moles | Feed to MA Reactor (1) Vol % | Feed to MA Scrubber Moles | Feed to MA Scrubber Vol % | Feed to CO Convertor Moles | Feed to CO Convertor Vol % | Feed to PSA Moles | Feed to PSA Vol % | Recycle Moles | Recycle Vol % | Vent From PSA Moles | Vent From PSA Vol % |
|---|---|---|---|---|---|---|---|---|---|---|---|---|---|---|
| n-Butane | 78.7 | 17.9 | 141.9 | 2.4 | 63.9 | 1.1 | 25.6 | 1.1 | 38.3 | 1.1 | 63.2 | 1.2 | 0.0 | 0.0 |
| i-Butane | 3.7 | 0.8 | 6.7 | 0.1 | 3.0 | 0.1 | 1.2 | 0.1 | 1.8 | 0.1 | 3.0 | 0.1 | 0.0 | 0.0 |
| $O_2$ | 353.9 | 80.5 | 445.4 | 7.5 | 119.9 | 2.0 | 48.0 | 2.1 | 71.9 | 2.1 | 91.5 | 1.7 | 0.0 | 0.0 |
| $N_2$ | 3.5 | 0.8 | 319.2 | 5.4 | 319.2 | 5.3 | 127.7 | 5.7 | 191.5 | 5.7 | 315.7 | 5.8 | 3.5 | 2.8 |
| Maleic Anhydride | 0.0 | 0.0 | 0.0 | 0.0 | 53.2 | 0.9 | 0.0 | 0.0 | 0.0 | 0.0 | 0.0 | 0.0 | 0.0 | 0.0 |
| CO | 0.0 | 0.0 | 111.6 | 1.9 | 167.8 | 2.8 | 67.1 | 3.0 | 100.7 | 3.0 | 111.6 | 2.0 | 0.0 | 0.0 |
| $CO_2$ | 0.0 | 0.0 | 4802.7 | 81.3 | 4849.5 | 80.9 | 1939.8 | 86.3 | 2909.7 | 86.3 | 4802.7 | 87.9 | 103.6 | 82.1 |
| $H_2O$ | 0.0 | 0.0 | 76.5 | 1.3 | 418.1 | 7.0 | 38.2 | 1.7 | 57.3 | 1.7 | 76.5 | 1.4 | 19.0 | 15.1 |
| TOTAL | 439.9 | 100.0 | 5904.1 | 100.0 | 5994.6 | 100.0 | 2247.5 | 100.0 | 3371.3 | 100.0 | 5464.2 | 100.0 | 126.1 | 100.0 |

(1) Sum of Fresh Feed and Recycle

Although the invention has been described with particular reference to a specific experiment, this experiment is merely exemplary of the invention and variations are contemplated. For example, the reaction can be carried out under conditions that will effect the production of other cyclic anhydrides, such as phthalic anhydride. Similarly, other catalysts and adsorbents and other means of gas separation can be used in the invention, if desired.

It is also understood that the invention is not limited to the equipment arrangement illustrated in the drawings. As noted above, the carbon monoxide converter 16 may be positioned upstream of the anhydride recovery unite 8, if desired. In fact, it may even by incorporated into reactor 2, either combined with the hydrocarbon oxidation catalyst in the form of a unitary mixed catalyst bed, or along as a separate bed. If it is incorporated into reactor 2 as a separate bed it is preferably located dwonstream of the hydrocarbon oxidation catalyst bed. It can be appreciated that the arrangement of the connecting fluid transfer lines for this version of the invention will be different from the arrangement illustrated in the drawings.

The scope of the invention is limited only the breadth of the appended claims:

We claim:

1. A process for the production of a cyclic anhydride comprising:
   (a) contacting in the vapor phase in a reaction zone a hydrocarbon selected from benzene, naphthaline, orthoxylene and four carbon straight-chain hydrocarbons and an oxygen-containing gas in the presence of a partial oxidation catalyst and carbon dioxide as an inert diluent under conditions which produce a gaseous product containing a cyclic anhydride and carbon monoxide;
   (b) removing said cyclic anhydride from the gaseous product;
   (c) converting carbon monoxide in the gaseous product to carbon dioxide, thereby producing a carbon monoxide-depleted gas stream;
   (d) removing part of the carbon dioxide from the carbon monoxide-depleted gas stream; and
   (e) recycling the remainder of the carbon monoxide-depleted gas stream to said reaction zone.

2. The process of claim 1 wherein carbon dioxide is present throughout the system as the principal inert diluent.

3. The process of claim 1, wherein said anhydride is maleic anhydride and said hydrocarbon is a straight-chain hydrocarbon containing four carbon atoms.

4. The process of claim 3, wherein said hydrocarbon is n-butane.

5. The process of claim 3, wherein said anhydride is phthalic anhydride and said hydrocarbon is orthoxylene.

6. The process of either of claims 1 or 2, wherein said oxygen-containing gas is substantially pure oxygen.

7. The process of either of claims 1 or 2, wherein said reaction zone is a reactor selected from the group consisting of fixed bed reactors, fluidized bed reactors, moving bed reactors and transport bed reactors.

8. The process of claim 7, wherein said reactor is a fixed bed reactor.

9. The process of either of claims 1 or 2, wherein the carbon monoxide is converted to carbon dioxide by means of a copper oxide-manganese oxide catalyst.

10. The process of either of claims 1 or 2, wherein the carbon dioxide is separated from said gaseous product by adsorption or absorption.

11. The process of claim 10, wherein the carbon dioxide is separated from said gaseous product by pressure swing adsorption.

12. The process of claim 11, wherein the unit in which said pressure swing adsorption is carried out contains an adsorbent selected rom silica gel, molecular sieves and mixtures of these.

13. A process for the production of an anhydride selected from phthalic anhydride and maleic anhydride comprising:
   (a) contacting in the vapor phase in a reaction zone a hydrocarbon selected from benzene, orthoxylene and straight-chain hydrocarbons containing 4 carbon atoms and substantially pure oxygen in the presence of an oxidation catalyst and carbon dioxide as the principal diluent under conditions which produce a gaseous product comprising said anhydride, unreacted hydrocarbon, carbon dioxide and carbon monoxide;
   (b) scrubbing said gaseous product with a liquid to remove anhydride from said gaseous product;
   (c) converting carbon monoxide in said gaseous product to carbon dioxide, thereby producing a carbon monoxide-depleted gas stream;
   (d) removing at least part of the unreacted hydrocarbon and part of the carbon dioxide from the carbon monoxide-depleted gas stream; and
   (e) recycling the separated unreacted hydrocarbon and carbon dioxide to said reaction zone; the carbon dioxide constituting at least 60 volume percent of the gaseous components present in the invention.

14. The process of claim 13, wherein said anhydride is maleic anhydride and said hydrocarbon is n-butane.

15. The process of claim 13, wherein said anhydride is phthalic anhydride and said hydrocarbon is o-xylene.

16. The process of claim 13, wherein said reaction zone is a fixed bed reactor.

17. The process of claim 13, wherein the carbon monoxide is converted to carbon dioxide by means of a copper oxide-manganese oxide catalyst.

18. The process of claim 13 wherein the amount of carbon dioxide present throughout the system in which said process is conducted is alone sufficiently high to prevent the existence of a flammable mixture.

19. The process of claim 13, wherein the unreacted hydrocarbon and carbon dioxide are separated from said gaseous product by adsorption or absorption or combinations of these.

20. The process of claim 19, wherein one or both of the unreacted hydrocarbon and carbon dioxide are separated from said gaseous product by pressure swing adsorption.

21. The process of claim 20, wherein the unit in which said pressure swing adsorption is carried out contains an adsorbant selected from silica gel, molecular sieve and mixtures of these.

22. The process of claim 19 wherein one or both of the unreacted hydrocarbon and carbon dioxide are separated from said gaseous product by absorption.

23. A process for the production of an anhydride selected from maleic anhydride and phthalic anhydride comprising:
   (a) contacting in the vapor phase in a reaction zone a hydrocarbon selected from benzene, orthoxylene and four carbon straight-chain hydrocarbons and substantially pure oxygen in the presence of an oxidation catalyst and carbon dioxide as the principal diluent under conditions which produce a gaseous product comprising said anhydride, unreacted hydrocarbon, carbon dioxide and carbon monoxide;

(b) removing said anhydride from said gaseous product;
(c) converting carbon monoxide in said gaseous product to carbon dioxide, thereby producing a carbon monoxide-depleted gas stream;
(d) purging part of the carbon monoxide-depleted gas stream; and
(e) recycling the remaining carbon monoxide-depleted gas stream to said reaction zone.

24. The process of claim 23, wherein said anhydride is maleic anhydride and said hydrocarbon is a four carbon straight-chain hydrocarbon.

25. The process of claim 24, wherein said hydrocarbon is n-butane.

26. The process of claim 2323 wherein said anhydride is phthalic anhydride and said hydrocarbon is o-xylene.

27. The process of claim 23, wherein the carbon monoxide is converted to carbon dioxide by means of a copper oxide-manganese oxide catalyst.

* * * * *